US007009015B2

United States Patent
Evain et al.

(10) Patent No.: US 7,009,015 B2
(45) Date of Patent: Mar. 7, 2006

(54) ALPHA-OLEFIN POLYMERIZATION CATALYST SYSTEM WHICH CONTAINS AN AROMATIC SILANE COMPOUND

(75) Inventors: Eric J. Evain, Wilmington, DE (US); Constantine A. Stewart, Wilmington, DE (US)

(73) Assignee: Basell Technology Company BV, (NL)

( * ) Notice: Subject to any disclaimer, the term of this patent is extended or adjusted under 35 U.S.C. 154(b) by 1229 days.

(21) Appl. No.: 09/742,868

(22) Filed: Dec. 21, 2000

(65) Prior Publication Data

US 2001/0016635 A1    Aug. 23, 2001

Related U.S. Application Data

(63) Continuation-in-part of application No. 09/469,508, filed on Dec. 22, 1999, now abandoned.

(51) Int. Cl.
*C08F 2/00*    (2006.01)
(52) U.S. Cl. ...................................... 526/194; 556/465
(58) Field of Classification Search ................ 526/194; 556/465
See application file for complete search history.

(56) References Cited

U.S. PATENT DOCUMENTS

| 4,180,636 A | 12/1979 | Hirota et al. ............... 526/125 |
| 4,242,479 A | 12/1980 | Yokota et al. ............... 526/124 |
| 4,347,160 A | 8/1982 | Epstein et al. ............... 252/429 |
| 4,382,019 A | 5/1983 | Greco .......................... 252/429 |
| 4,435,550 A | 3/1984 | Ueno et al. ................... 526/73 |
| 4,442,276 A | 4/1984 | Kashiwa et al. ............. 526/125 |
| 4,472,524 A | 9/1984 | Albizzati .................... 502/113 |
| 4,473,660 A | 9/1984 | Albizzati et al. ............ 502/124 |
| 4,522,930 A | 6/1985 | Albizzati et al. ............ 502/124 |
| 4,530,912 A | 7/1985 | Pullukat et al. ............. 502/104 |
| 4,560,671 A | 12/1985 | Gross et al. ................. 502/105 |
| 4,581,342 A | 4/1986 | Johnson et al. ............. 502/119 |
| 4,657,882 A | 4/1987 | Karayannis et al. ........ 502/115 |
| 5,102,842 A | 4/1992 | Smith et al. ................ 502/124 |

FOREIGN PATENT DOCUMENTS

| EP | 0045976 | 2/1982 |
| EP | 0045977 | 2/1982 |
| EP | 0320150 | 6/1989 |
| EP | 0658577 | 6/1995 |
| JP | SHO 447392 | 4/1969 |
| JP | HEI 07118320 | 5/1995 |
| JP | 10130280 | 5/1998 |
| WO | 9730096 | 8/1997 |

*Primary Examiner*—Samuel Barts

(57) ABSTRACT

Aromatic silane compounds containing at least an aromatic ring bound directly to the silicon atom, wherein the aromatic ring has at least one substituent located in the ortho position selected from $C_{1-10}$ hydrocarbon groups, are useful as electron donors in olefin polymerization catalysts for the production of polyolefins having a stereoblock content of from about 7 to about 25%.

15 Claims, No Drawings

ALPHA-OLEFIN POLYMERIZATION CATALYST SYSTEM WHICH CONTAINS AN AROMATIC SILANE COMPOUND

This is a continuation-in-part of application Ser. No. 09/469,508, filed on Dec. 22, 1999 now abandoned.

BACKGROUND OF THE INVENTION

This invention relates to aromatic silane compounds and to Ziegler-Natta catalyst systems which use said aromatic silane compounds as electron donors for the production of olefin polymers. The olefin polymers produced with such catalyst systems exhibit a desirable stereoblock content of from about 7 to about 25%.

Polymer stereoblock content can affect the physical properties of the polymer itself and those of products prepared therefrom, particularly films manufactured from such polyolefins and blends of such polyolefins with elastomeric materials, regardless of whether they are mechanically blended from pre-produced polyolefins and elastomeric materials or reactor blended by first producing such a polyolefin then producing the elastomeric material in the presence of the polyolefin.

Organosilane compounds have been used in catalysts (1) as an internal electron donor in a solid catalyst component comprising a halogen-containing titanium compound supported on an activated magnesium dihalide compound and (2) as an external electron donor in combination with an aluminum-alkyl co-catalyst. Typically the organosilane compounds have Si—OR, Si—OCOR or Si—NR$_2$ groups, where R is alkyl, alkenyl, aryl, arylalkyl or cycloalkyl having 1 to 20 atoms. Such compounds are described in U.S. Pat. Nos. 4,180,636; 4,242,479; 4,347,160; 4,382,019; 4,435,550; 4,442,276; 4,473,660; 4,530,912 and 4,560,671, where they are used as internal electron donors in the solid catalyst component; and in U.S. Pat. Nos. 4,472,524, 4,522,930, 4,560,671, 4,581,342, 4,657,882 and European patent application Nos. 45976 and 45977, where they are used as external electron donors with the aluminum-alkyl co-catalyst.

Conventional propylene homopolymers, obtained by using external electron donors known in the state of the art, show a high degree of cristallinity, which determines the physical properties of the polymers, such as high melting temperature, high glass temperature and high $\Delta H_{fus}$. These physical properties, while necessary in some applications, are often disadvantageous in fiber and film applications, where lower bonding temperatures are required, for instance in producing laminate structures.

Hence, there is the need for external electron donor compounds which allow propylene polymers to be obtained having a relatively high degree of stereoblocks, at the same time at acceptable polymerization yields.

SUMMARY OF THE INVENTION

It has been surprisingly found that a novel class of substituted aromatic silane compounds can be used as external electron donors for olefin polymerization catalyst systems, in order to produce propylene polymers having a stereoblock content of from about 7 to about 25%.

In one aspect, the present invention concerns an aromatic silane compound useful as electron donor compound in an olefin polymerization catalyst, having formula (I):

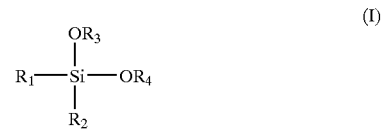

wherein $R_1$ is selected from the group consisting of linear or branched $C_{1-26}$ alkyl, $C_{2-26}$ alkenyl, $C_{1-26}$ alkoxy, $C_{2-26}$ alkoxyalkyl, $C_{7-26}$ arylalkyl, $C_{3-26}$ cycloalkyl and $C_{4-26}$ cycloalkoxy groups, optionally containing one or more halogen atoms;

$R_2$ is an aromatic ring having at least one substituent in the ortho position selected from $C_{1-10}$ hydrocarbon groups; and $R_3$ and $R_4$, the same or different from each other, are selected from the group consisting of a linear or branched $C_{1-10}$ alkyl and $C_{3-10}$ cycloalkyl groups.

In another aspect, the present invention concerns a catalyst system for the polymerization of olefins comprising:

(A) an aromatic silane compound having formula (I):

wherein $R_1$ is selected from the group consisting of linear or branched $C_{1-26}$ alkyl, $C_{2-26}$ alkenyl, $C_{1-26}$ alkoxy, $C_{2-26}$ alkoxyalkyl, $C_{7-26}$ arylalkyl, $C_{3-26}$ cycloalkyl and $C_{4-26}$ cycloalkoxy groups, optionally containing one or more halogen atoms;

$R_2$ is an aromatic ring having at least one substituent in the ortho position; and $R_3$ and $R_4$, the same or different from each other, are selected from the group consisting of a linear or branched $C_{1-10}$ alkyl and $C_{3-10}$ cycloalkyl groups;

(B) an aluminum alkyl compound; and (C) a solid catalyst component comprising Mg, Ti, halogen and an electron donor compound.

In another aspect, this invention concerns a process for the polymerization of alpha-olefins carried out in the presence of the catalyst system described above, to produce a polyolefin having a stereoblock content of from about 7 to about 25%, and preferably from 12 to 20%.

DETAILED DESCRIPTION OF THE PREFERRED EMBODIMENTS

The inventors have discovered that organosilanes having an aromatic ring substituted in the ortho position can produce, in conjunction with the catalyst systems described below, polyolefin resins having a stereoblock content of from about 7 to about 25%.

The aromatic silane compounds of the present invention have the following formula (I):

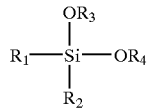

wherein $R_1$, $R_2$, $R_3$ and $R_4$ have the meanings reported above.

In one preferred embodiment of the present invention, $R_1$ is a linear or branched $C_{1-18}$ alkyl or $C_{3-18}$ cycloalkyl, and even more preferably $R_1$ is a linear $C_{1-5}$ alkyl or a branched $C_{3-8}$ alkyl.

$R_2$ is an aromatic ring having at least one substituent in the ortho position selected from $C_{1-10}$ hydrocarbon groups. Depending on the stereoblock content desired, $R_2$ may preferably be a non-heterocyclic aromatic system, and most preferably a mono-substituted phenyl ring system, a di-substituted phenyl ring system, or a mono-substituted naphthyl ring system.

By "substituent in the ortho position", it is meant that at least one of the two aromatic ring atoms adjacent to the aromatic ring atom that is bound to the silicon atom must be substituted.

The groups $R_3$ and $R_4$, the same or different from each other, are preferably $C_{1-10}$ alkyl, and even more preferably are methyl or ethyl.

Illustrative examples of aromatic silanes which conform to formula (I) include the following:
(2-ethylphenyl)-3,3-dimethylbutyl-dimethoxysilane;
(2-ethylphenyl)-3-methylbutyl-dimethoxysilane;
(2-ethylphenyl)-propyl-dimethoxysilane;
(2-ethylphenyl)-3,3,3-trifluoropropyl-dimethoxysilane;
(2-methylphenyl)-propyl-dimethoxysilane; and
(2,6-dimethylphenyl)-propyl-dimethoxysilane.

The aromatic silanes of the present invention may be prepared from readily available starting materials using conventional synthesis methods and equipment well known to those of ordinary skill in the art. Aromatic silanes where the aromatic ring system is an ortho-substituted phenyl group may be prepared by the reaction between the appropriate 2-phenylmagnesium bromide and the appropriate alkyl-trialkoxysilane, as illustrated in Example 2. Alternatively, such ortho-substituted aromatic silanes may be prepared by first reacting the appropriate 2-bromobenzene with an alkyl lithium reagent, such as n-butyl lithium, to generate the corresponding 2-phenyl lithium, which is then allowed to react with the appropriate alkyl-trialkoxysilane, as illustrated in Example 3.

The organosilanes of the present invention are useful as the external electron donor in an olefin polymerization catalyst system. More particularly, the present invention concerns a catalyst system for the polymerization of olefins comprising:

(A) an aromatic silane compound having formula (I):

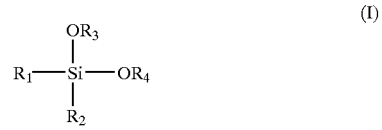

wherein
$R_1$ is preferably a linear or branched $C_{1-8}$ alkyl or $C_{3-18}$ cycloalkyl, and even more preferably $R_1$ is a linear $C_{1-5}$ alkyl;
$R_2$ is an aromatic ring having at least one substituent in the ortho position;
$R_3$ and $R_4$, the same or different from each other, are preferably $C_{1-10}$ alkyl groups, and even more preferably are methyl or ethyl;
(B) an aluminum alkyl compound; and
(C) a solid catalyst component comprising Mg, Ti, halogen and an electron donor compound as essential elements.

In said aromatic silane compound (A), $R_1$ is preferably selected from the group consisting of linear or branched $C_{1-18}$ alkyl, $C_{1-18}$ alkoxyl and $C_{3-18}$ cycloalkyl groups, and even more preferably $R_1$ is selected from the group consisting of linear $C_{1-5}$ alkyl and branched $C_{3-8}$ alkyl groups.

$R_2$ is preferably selected from the group consisting of mono-substituted phenyl, di-substituted phenyl and mono-substituted naphthyl, and the ortho substituent is preferably a linear or branched $C_{1-10}$ alkyl or $C_{1-10}$ alkoxy group.

$R_3$ and $R_4$ are preferably selected from the group consisting of linear or branched $C_{1-8}$ alkyl and $C_{3-8}$ cycloalkyl, and even more preferably are methyl or ethyl.

The aluminum alkyl compound (B) may be triethylaluminum, isobutylaluminum, tri-n-butylaluminum, and linear and cyclic alkylaluminum compounds containing two or more aluminum atoms linked to one another through oxygen or nitrogen atoms or $SO_4$ or $SO_3$ groups. Examples of such alkyl aluminum compounds include $(C_2H_5)_2Al$—O—$Al(C_2H_5)$; $(C_2H_5)_2Al$—$N(C_6H_5)$—$Al(C_2H_5)$; $(C_2H_5)_2Al$—$SO_2$—$Al(C_2H_5)$; $CH_3[(CH_3Al$—O—$]_nAl(CH_3)_n$; and $(CH_3Al$—O—$]_n$. The alkyl aluminum compound (B) is preferably triethylaluminum.

The solid catalyst component (C) preferably comprises a titanium compound having at least one titanium-halogen bond and an internal electron donor, both supported on an active magnesium halide.

The titanium compound, which may be selected from titanium tetrahalides and titanium alkoxy halides, is supported on the solid magnesium halide, according to common procedures. The titanium compound is preferably $TiCl_4$.

The magnesium halide is in anhydrous state, and preferably has a water content of less than 1% by weight. The magnesium halide is preferably $MgCl_2$ or $MgBr_2$, with $MgCl_2$ being most preferred.

Those of ordinary skill in this art are well aware how to activate the magnesium dihalide compound, and to determine its degree of activation. More particularly, the active magnesium halides forming the support of component (C) are the Mg halides showing in the X-ray powder spectrum of component (C) a broadening of at least 30% of the most intense diffraction line which appears in the powder spectrum of the corresponding inactivated magnesium halide having 1 m²/g of surface area or are the Mg dihalides showing an X-ray powder spectrum in which said most intense diffraction line of the inactivated magnesium dihalide is absent and is replaced by a halo with an intensity peak shifted with respect to the interplanar distance of the most intense diffraction line and/or are the Mg dihalides having a surface area greater than 3 m$^2$/g.

The measurement of the surface area of the Mg halides is made on component (C) after treatment with boiling TiCl$_4$ for 2 hours. The value found is considered as the surface area of the Mg halide.

The Mg dihalide may be preactivated, may be activated in situ during the titanation, may be formed in situ from a Mg compound, which is capable of forming Mg dihalide when treated with a suitable halogen-containing transition metal compound, and then activated, or may be formed from a Mg dihalide C$_{1-3}$ alkanol adduct wherein the molar ratio of MgCl$_2$ to alcohol is 1:1 to 1:3, such as MgCl$_2$.3ROH where R is a C$_{1-20}$ linear or branched alkyl, C$_{6-20}$ aryl or C$_{5-20}$ cycloalkyl.

Very active forms of Mg dihalides are those showing an X-ray powder spectrum in which the most intense diffraction line appearing in the spectrum of the corresponding inactivated magnesium halide having 1 m$^2$/g of surface area is decreased in relative intensity and broadened to form a halo or are those in which said most intense line is replaced by a halo having its intensity peak shifted with respect to the interplanar distance of this most intense line. Generally, the surface area of the above forms is higher than 30–40 m$^2$/g and is comprised, in particular, between 100–300 m$^2$/g.

Active forms are also those derived from the above forms by heat-treatment of component (C) in inert hydrocarbon solvents and showing in the X-ray spectrum sharp diffraction lines in place of halos. The sharp, most intense line of these forms shows, in any case, a broadening of at least 30% with respect to the corresponding line of inactivated Mg dihalides having 1 m$^2$/g of surface area.

The internal electron donor may be selected from alkyl, aryl, and cycloalkyl esters of aromatic acids, especially benzoic acid or phthalic acid and their derivatives, such as ethyl benzoate, n-butyl benzoate, methyl p-toluate, methyl p-methoxybenzoate, and diisobutylphthalate. Alkyl or alkaryl ethers, ketones, mono- or polyamines, aldehydes and phosphorus compounds, such as phosphines and phosphoramides, can also be used as the internal electron donor. The phthalic acid esters are most preferred.

Solid catalyst component (C) can be prepared using techniques and equipments well known to those of ordinary skill in the art. For example, the magnesium halide, titanium compound and the internal electron donor can be milled under conditions where the magnesium halide is active. The milled product is then treated one or more times with an excess of TiCl$_4$ at a temperature of from 80° to 135° C. and then washed with a hydrocarbon such as hexane until all chlorine ions have been removed.

Alternatively, the solid catalyst component (C) may be prepared by first preactivating the magnesium chloride according to known methods, reacting it with an excess of TiCl$_4$ containing the internal electron donor in solution at a temperature of from 80° to 135° C., and then washing the solid with a hydrocarbon such as hexane to remove residual TiCl$_4$.

Yet another method for preparing the solid catalyst component (C) includes reacting a MgCl$_2$nROH adduct (where R is a C$_{1-20}$ linear or branched alkyl, C$_{6-20}$ aryl or C$_{5-20}$ cycloalkyl), preferably in the form of spheroidal particles, with an excess of TiCl$_4$ containing the internal electron donor in solution at a temperature of from 80° to 120° C., isolating the solid, reacting it once more with TiCl$_4$ and then washing the solid with a hydrocarbon, such as hexane, to remove all remaining chlorine ions.

The molar ratio between the Mg dihalide and the halogenated Ti compound supported thereon is preferably between 1 and 500, while the molar ratio between the halogenated Ti compound and the internal electron donor supported on the Mg dihalide is preferably between 0.1 and 50. The amount of aluminum alkyl compound (B) employed is generally such that an aluminum/titanium ratio is from 1 to 1000.

The catalyst system comprising an aromatic silane compound (A), an aluminum alkyl compound (B) and a solid catalyst component (C) can be added to the polymerization reactor by separate means substantially simultaneously, regardless of whether the monomer is already in the reactor, or sequentially if the monomer is added to the polymerization reactor later. It is preferred to premix components (A) and (B), then contact said premix with component (C) prior to the polymerization for from 3 minutes to about 10 minutes at ambient temperature.

The alpha olefin monomer can be added prior to, with or after the addition of the catalyst to the polymerization reactor. It is preferred to add it after the addition of the catalyst.

Another object of the instant invention is a process for the polymerization of alpha-olefins carried out in the presence of the catalyst system as described above.

The polymerization reactions can be done in slurry, liquid or gas phase processes, or in a combination of liquid and gas phase processes using separate reactors, all of which can be done either by batch or continuously.

The polymerization is generally carried out at a temperature of from 0 to 150° C., and preferably from 40 to 90° C.; the polymerization may be carried out at atmospheric pressure or at higher pressures, preferably from 100 to 10,000 kPa, and more preferably from 200 to 8,000 kPa.

Chain terminating agents, such as hydrogen, can be added as needed to reduce the molecular weight of the polymer, according to methods well known in the state of the art.

The catalysts may be precontacted with small quantities of olefin monomer (prepolymerization), maintaining the catalyst in suspension in a hydrocarbon solvent and polymerizing at a temperature of 60° C. or below for a time sufficient to produce a quantity of polymer from 0.5 to 3 times the weight of the solid catalyst component.

This prepolymerization also can be done in liquid or gaseous monomer to produce, in this case, a quantity of polymer up to 1000 times the catalyst component weight.

Suitable alpha-olefins which can be polymerized by this invention include olefins of the formula CH$_2$=CHR, where R is H or C$_{1-20}$ straight or branched alkyl, such as ethylene, propylene, butene-1, pentene-1, 4-methylpentene-1 and octene-1.

The aromatic silane compounds of the present invention, as well as the polymerization catalyst systems containing them, enable the production of propylene polymers, and in particular propylene homopolymer having a stereoblock content of from about 7 to about 25%, and preferably from 12 to 20%, by changing the ortho substituent on the aromatic ring of the silane themselves.

Propylene polymers prepared using the external electron donors of the present invention may be manufactured into films using conventional apparatus and techniques well known to those of ordinary skill in the polyolefin art.

EXAMPLES

The examples below illustrate specific embodiments of the invention, and are not intended to limit the scope of the invention in any manner whatsoever.

General Procedures and Characterizations

Purity of all reagents was confirmed by either chromatographic or spectrophotometric analysis. Where appropriate, reagents were purified prior to use. All nonaqueous reactions were performed under an atmosphere of dry nitrogen or argon using glassware that was dried under vacuum while heated. Air and moisture sensitive solutions were transferred via syringe or stainless steel cannula. Reported boiling points and melting points were uncorrected.

NMR spectra were recorded on a Varian Unity 300 spectrometer operating at 300 MHz and are referenced internally to either tetramethylsilane or residual proton impurities. Data for $^1H$ are reported as follows: chemical shift, ($\delta$, ppm), multiplicity (s-singlet; d-doublet; t-triplet; q-quartet, qn-quintet; m-multiplet), integration. Data for $^{13}C$ NMR are reported in terms of chemical shift ($\delta$, ppm).

Infrared spectra were reported on a BioRad FT430 series mid-IR spectrometer using KBr plates and are reported in terms of frequency of absorption ($v$, $cm^{-1}$).

Gas chromatographic analyses were conducted using a Hewlett Packard model 6890 chromatograph using flame ionization detection ("FID") coupled to a model HP6890 integrator. In a typical analysis 1.0 $\mu$L was injected into a 250° C. injector (50:1 split ratio; 10 psi column head pressure, 106 mL/min split flow; 111 mL/min total flow). Helium was used as a carrier gas through an Alltech Heliflex AT-1 column (30 m×0.32 mm×0.3 $\mu$m). The initial temperature was held at 50° C. for two minutes then increased at 10° C./min to a final temperature of 300° C. The FID detector was held at 300° C. (40 mL/min $H_2$; 400 mL/min air; constant make-up mode using 30 mL/min He).

Two GC/MS systems were used. One system was a Hewlett Packard model 5890 GC coupled to a Hewlett Packard model 5970 mass selective detector. In a typical analysis, 2.0 $\mu$L of sample was injected into a 290° C. splitless injection port. Helium was used as the carrier gas through an HP-1 column (Hewlett Packard, 25 m×0.33 mm×0.2 $\mu$m). The initial temperature was held at 75° C. for four minutes. The column was warmed at 10° C./min. Mass acquisition was 10–800 AMU. The spectra are reported as m/z (relative abundance).

The second GC/MS system was a Hewlett Packard model 6890 GC coupled to a Hewlett Packard model 5973 mass selective detector. In a typical analysis, 1.0 $\mu$L of sample was injected into a 290° C. split/splitless injection port. Helium was used as the carrier gas through an HP-5 column (Hewlett Packard, 30 m×0.25 mm×0.25 $\mu$m). The initial temperature was held at 50° C. for four minutes. The column was warmed at 10° C./min. Mass acquisition was 10–800 AMU. The spectra are reported as m/z (relative abundance).

Temperature Rising Elution Fractionation technique (TREF) was used to analyze the crystalline structure of the polymers. The technique uses xylene as a solvent to dissolve the polymer crystal structure and determines the dissolved amount as the temperature is raised above room temperature up to a point where all of the polymer is dissolved. The portion dissolved at room temperature is designated as atactic; the portion dissolved between room temperature and 100° C. is designated as stereoblock, and the remaining portion above 100° C. is called isotactic.

Synthesis of Aromatic Silane Compounds

Example 1

Synthesis of (2-ethylphenyl)-propyl-dimethoxysilane

A 500 mL round bottomed flask was charged with magnesium turnings (2.73 g, 112 mmol, Aldrich) and ether (300 mL, Aldrich). Bromo-2-ethylbenzene (18.7 mL, 135 mmol, Aldrich) was added over 30 minutes. The reaction stirred for three hours at room temperature and became dark brown in color. The contents were refluxed for one hour.

The contents were cooled to 0° C. and propyl-trimethoxysilane (19.8 mL, 112 mmol) was added over 25 minutes. The reaction was stirred at room temperature overnight (18 hours) during which time a white precipitate formed. The contents were poured into water (500 mL), the layers separated and the product extracted into ether (3×150 mL). The combined organic portions were dried ($MgSO_4$), filtered and the solvent removed via rotary evaporation providing 28.9 g crude material. Distillation under reduced pressure (b.p. 89° C., 0.7 mm Hg) produced (2-ethylphenyl)-propyl-dimethoxysilane (12.2 g, 51.3 mmol, 45.8% yield); $C_{13}H_{22}SiO_2$: (Mw=238.40); $^1H$ NMR ($CDCl_3$) $\delta$ 7.7 (m, 1H), 7.4–7.1 (m, 3H), 3.5 (s, 6H), 2.8 (q, 2H), 1.4 (m, 2H), 1.2 (t, 3H), 0.9–0.8 (m, 5H); $^{13}C$ NMR ($CDC_3$) $\delta$ 150.5, 135.8, 131.3, 130.3, 128.0, 124.9, 50.3, 28.6, 17.7, 16.3, 15.9, 0.1; IR (capillary film) $v$ 3054, 2966, 2874, 2836, 1590, 1460, 1192, 1128, 1104, 998, 809, 752; MS m/z (relative abundance) 238 (6.5), 195 (100), 163 (58.8), 133 (28.6), 105 (10.7), 91 (14.9), 59 (23.7).

Comparative Example 1

Synthesis of (phenyl)-propyl-dimethoxysilane

A 500 mL round bottomed flask was charged with propyl-trimethoxysilane (19.3 mL, 1.10×10$^{-1}$ mole, Hüls) and ether (250 mL, Aldrich). A pressure equalizing addition funnel was charged with phenylmagnesium bromide (33.3 mL of a 3M solution in ether, 99.9 mmol, Aldrich) and ether (50 mL). The contents of the addition funnel were added into the silane over a 20 minute period (exotherm). A white precipitate formed. The reaction was stirred for two hours at room temperature then poured into 0.2N HCl (300 mL). The layers were separated, the product extracted into ether (2×250 mL), dried ($MgSO_4$), and filtered. The solvent was removed via rotary evaporation resulting in 23.5 grams of crude material. Distillation under reduced pressure (b.p. 71° C., 0.6 mm Hg) provided phenyl-propyl-dimethoxysilane (18.5 g, 88.0 mmol, 88% yield); $C_{11}H_{18}SiO_2$ (mw=210.34); $^1H$ NMR ($CDCl_3$) $\delta$ 7.7 (m, 2H), 7.4 (m, 3H), 3.6 (s, 6H), 1.4 (m, 2H), 1.0 (t, 3H), 0.9 (t, 2H); $^{13}C$ NMR ($CDCl_3$) $\delta$ 134.3, 133.3, 130.1, 127.9, 50.6, 17.9, 16.3, 14.8; MS m/z (relative abundance) 210 (2), 167 (100), 137 (33), 107 (17), 91 (17), 59 (10).

Example 2

Synthesis of (2-ethylphenyl)-3-methylbutyl-dimethoxysilane

A 1000 mL round bottomed flask was charged with magnesium turnings (1.97 g, 81.0 mmol, Aldrich) and ether (500 mL, Aldrich). Bromo-2-ethylbenzene (14.0 mL, 101 mmol, Aldrich) was added over 30 minutes. The reaction stirred for three hours at room temperature and became dark brown in color. The contents were refluxed for one hour. The contents were cooled to 0° C. and isoamyl-trimethoxysilane (15.9 g, 82.8 mmol, previously prepared by reaction between isoamyl magnesiumbromide and tetramethylorthosilicate) was added over 25 minutes. The reaction was stirred at room temperature overnight (18 hours) during which time a white precipitate formed. The contents were poured into water (500 mL), the layers separated and the product extracted into ether (3×150 mL). The combined organic portions were dried (MgSO$_4$), filtered and the solvent removed via rotary evaporation providing 29.6 g crude material. Distillation under reduced pressure (b.p. 109° C., 1.1 mm Hg) produced (2-ethylphenyl)-3-methylbutyl-dimethoxysilane (7.68 g, 28.8 mmol, 35.6% yield); $C_{15}H_{26}SiO_2$ (Mw=266.45); $^1$H NMR (CDCl$_3$) δ 7.7 (m, 1H), 7.3 (m, 1H), 7.2 (m, 2H), 3.5 (s, 6H), 2.8 (q, 2H), 1.4 (m, 1H), 1.2 (m, 5H), 0.8 (m, 8H); $^{13}$C NMR (CDCl$_3$) δ 150.5, 135.9, 131.2, 130.3, 128.0, 124.9, 50.3, 31.5, 30.7, 28.6, 21.9, 16.1, 10.9; IR (capillary film) v 3054, 2974, 1590, 1467, 1370, 1200, 1118, 1023, 936, 874, 803, MS m/z (relative abundance) 266 (0.02), 195 (100), 163 (59.1), 160 (28.8), 133 (25.5), 105 (11.2), 91 (12.3), 59 (18.4).

Comparative Example 2

(Phenyl)-3-methylbutyl-dimethoxysilane was synthesized according to the procedure reported in Example 2, but using bromo-benzene instead of bromo-2-ethylbenzene.

Example 3

Synthesis of (2,4-dimethoxyphenyl)-propyl-dimethoxysilane

A 500 mL round bottomed flask was charged with hexane (200 mL, Aldrich) and bromo-2,4-dimethoxybenzene (12.2 g, 56.0 mmol, Aldrich). The contents were cooled to 0° C. and n-butyl lithium (34.7 mL of a 1.6M solution in hexanes, 55.5 mmol, Aldrich) was added over 15 minutes (white precipitate). The contents were stirred at room temperature for ninety (90) minutes. The solution was added, via cannula, into a 1000 mL round bottomed flask containing hexane (300 mL, Aldrich) and propyl-trimethoxysilane (9.8 mL, 56 mmol). The reaction was stirred at room temperature overnight (18 hours). Ethanol (10 mL, Aldrich) was added to quench residual base. The contents were poured into 0.2N HCl (250 mL). The layers were separated and the product extracted into ether (2×150 mL). The combined organic portions were dried (MgSO$_4$), filtered, and the solvent removed via rotary evaporation (16.2 g crude). Distillation under reduced pressure (b.p. 115° C., 0.04 mm Hg) provided 2,4-dimethoxyphenyl-propyl-dimethoxysilane (9.13 g, 33.8 mmol, 61% yield); $C_{13}H_{22}O_4Si$ (Mw=270.40); $^1$H NMR (CDCl$_3$) δ 7.5 (d, 1H), 6.5 (m, 1H), 6.4 (d, 1H), 3.8 (s, 3H), 3.8 (s, 3H), 3.5 (s, 6H), 1.4 (m, 2H), 0.9 (t, 3H), 0.8 (t, 2H); $^{13}$C NMR (CDCl$_3$) δ 165.8, 163.2, 137.6, 112.7, 104.6, 97.5, 55.0, 54.9, 50.4, 17.7, 16.2, 15.4; IR (capillary film) v 2950, 2836, 1596, 1571, 1460, 1299, 1206, 1154, 1089, 1036; MS m/z (relative abundance) 270 (11.1), 227 (45.6), 197 (100), 167 (24.4), 137 (10.9), 121 (22.6), 91 (9.9), 59 (18.4).

Comparative Example 3

(4-Methoxyphenyl)-propyl-dimethoxysilane was synthesized according to the procedure reported in Example 3, but using bromo-4-dimethoxybenzene instead of bromo-2,4-dimethoxybenzene.

Example 4

(2-Methoxynaphthyl)-propyl-dimethoxysilane was synthesized according to the procedure reported in Example 3, but using bromo-2-methoxynaphthalene instead of bromo-2,4-dimethoxybenzene.

Example 5

Synthesis of (2,6-dimethylphenyl)-propyl-dimethoxysilane

A 500 mL round bottomed flask was charged with magnesium powder (2.1 g, 86 mmol, Aldrich) and ether (250 mL, Aldrich). 2-Bromo-m-xylene (9.0 mL, 68 mmol, Aldrich) was added over a 25 minute period. The contents were refluxed overnight (18 hours). The brown solution was cooled to room temperature and propyl-trimethoxysilane (17.8 mL, 101 mmol) was added over 20 minutes. A white precipitate formed. The contents were stirred at room temperature overnight (18 hours). The reaction was poured into 0.2N aqueous HCl (500 mL), the layers were separated and the product extracted into ether (3×150 mL). The combined organic portions were dried (MgSO$_4$), filtered, and the solvent removed via rotary evaporation (13.5 g crude). Distillation under reduced pressure (b.p. 57° C., 0.04 mm Hg) provided (2,6-dimethylphenyl)-propyl-dimethoxysilane (6.8 g, 28 mmol, 41% yield); $C_{13}H_{22}SiO_2$ (Mw=238.40); $^1$H NMR (CDCl$_3$) δ 7.2 (t, 1H), 7.0 (d, 2H), 3.6 (s, 6H), 2.5 (s, 6H), 1.4 (m, 2H), 1.0 (t, 3H), 0.9 (t, 2H); $^{13}$C NMR (CDCl$_3$) δ 145.2, 131.0, 129.6, 128.0, 49.8, 23.4, 17.9, 16.7, 16.3; MS m/z (relative abundance) 238 (8), 195 (100), 165 (22), 133 (12), 119 (10), 105 (13), 91 (9), 59 (16).

Comparative Examples 4–6

The silane compounds (4-methyl-phenyl)-propyl-dimethoxysilane, (4-propyl-phenyl)-propyl-dimethoxysilane and (4-chloro-phenyl)-propyl-dimethoxysilane were synthesized according to the procedure reported in Example 2, but using respectively bromo-4-methyl-benzene, bromo-4-propyl-benzene and bromo-4-chloro-benzene instead of bromo-2-ethylbenzene.

Example 6

Synthesis of (2-ethyl-phenyl)-3,3-dimethylbutyl-dimethoxysilane

Under an atmosphere of dry nitrogen a magnetically stirred suspension of anhydrous tetrahydrofuran (Aldrich, 300 mL) and magnesium turnings (Aldrich, 1.2 g, 49 mmol) was treated dropwise at room temperature with 1-bromo-2-ethylbenzene (Aldrich, 6.1 mL, 44 mmol). After minutes the reaction mixture began to reflux mildly. After the addition was complete the reaction mixture was heated to reflux overnight (18 h). A separate flask was flushed with dry nitrogen and then charged with anhydrous tetrahydrofuran (Aldrich, 100 mL) and 3,3-dimethylbutyl-trimethoxysilane (Huls, 11.4 mL, 49 mmol). The Grignard solution was cooled to room temperature and then added to the silane solution at room temperature via stainless steel cannula. The reaction mixture stirred at room temperature overnight (18 h). Ethyl alcohol (Aldrich, 5 mL) was added to quench any remaining Grignard. The reaction mixture was concentrated on a rotary evaporator and distilled in vacuum to give 3.7 g (30%) of the title compound as a colorless oil (b.p. 107–108° C. at 0.5 mm Hg, 99% GC-purity): $C_{16}H_{28}O_2Si$ (Mw=280).

Propylene Polymerization

Preparation of the Solid Catalyst Component

Into a 500 mL four-necked round flask, purged with nitrogen, 250 mL of $TiCl_4$ were introduced at 0° C. While stirring, 10.0 g of microspheroidal $MgCl_2 \cdot 2.8C_2H_5OH$ (prepared according to the method described in example 2 of U.S. Pat. No. 4,399,054, but operating at 3000 rpm instead of 10000 rpm) and 7.4 mmol of diisobutylphthalate were added. The temperature was raised to 100° C. and maintained for 120 minutes. Then the stirring was discontinued, the solid product was allowed to settle and the supernatant liquid was siphoned off. 250 mL of fresh $TiCl_4$ were then added. The mixture was reacted at 120° C. for 60 min and, then, the supernatant liquid was siphoned off. The solid was washed six times with anhydrous hexane (6×100 mL) at 60° C.

Polymerization Procedure

A polymerization reactor was heated to 70° C. and purged with a slow argon flow for 1 hour; its pressure was then raised to 100 psig with argon, at 70° C., and the reactor was vented. This procedure was repeated 4 more times. The reactor was then cooled to 30° C.

Separately, into an argon purged addition funnel, the following were introduced in the order they are listed: 75 mL of hexane, 4.47 mL of a 1.5M solution of triethylaluminum (TEAL) (0.764 g, 6.70 mmol) in hexane, about 0.340 mmol of an aromatic silane compound, as indicated in the following examples (so that the molar ratio of TEAL:organosilane equaled approximately 20:1), and the obtained mixture was allowed to stand for 5 minutes. Of this mixture, 35 mL were added to a flask. Then 0.0129 g of the solid catalyst component, prepared as described above, were added to the flask and mixed by swirling for a period of five minutes. The catalytic complex so obtained was introduced, under an argon purge, into the above polymerization reactor at room temperature. The remaining hexane/TEAL/silane solution was then drained from the addition funnel to the flask, the flask was swirled and drained into the reactor and the injection valve was closed. The polymerization reactor was slowly charged with 2.2 L of liquid propylene, under stirring, and 0.25 mole percent of $H_2$ were introduced. The reactor was then heated to 70° C. and the polymerization was carried out for about 2 hours, at constant temperature and pressure. After about 2 hours under stirring, the polymerization was stopped and the remaining propylene was slowly vented. The reactor was heated to 80° C., purged with argon for 10 minutes and then cooled to room temperature and opened. The polymer was removed and dried in a vacuum oven at 80° C., for 1 hour.

Examples 7–11 and Comparative Examples 7–12

In Examples 7–11, polypropylene polymers were prepared in accordance with the polymerization procedure reported above, using the organosilane compounds synthesized in the previous examples as the external electron donor in otherwise identical catalyst systems.

In Comparative Examples 7–12, the same polymerization procedure was carried out by using aromatic silane compounds wherein the aromatic ring does not bear any substituents in the ortho position.

The aromatic silane compounds used in the polymerization, as well as the stereoblock content of the resultant polymer and the polymerization yields are reported in Table 1.

TABLE 1

| Example | Silane compound | Stereo-block (% wt.) | Yield (kg/g$_{cat}$) |
|---|---|---|---|
| Example 7 | (2-ethylphenyl)-propyl-dimethoxysilane | 13.3 | 45.2 |
| Comp. Ex. 7 | phenyl-propyl-dimethoxysilane | 8.0 | 46.7 |
| Example 8 | (2-ethylphenyl)-3-methylbutyl-dimethoxysilane | 19.7 | 40.1 |
| Comp. Ex. 8 | phenyl-3-methylbutyl-dimethoxysilane | 19.0 | 30.2 |
| Example 9 | (2,4-dimethoxyphenyl)-propyl-dimethoxysilane | 14.9 | 24.3 |
| Comp. Ex. 9 | (4-methoxyphenyl)-propyl-dimethoxysilane | 10.9 | 28.5 |
| Example 10 | (2-methoxynaphthyl)-propyl-dimethoxysilane | 21.4 | 20.8 |
| Example 11 | (2-ethyl-phenyl)-3,3-dimethylbutyl-dimethoxysilane | 20.4 | 34.2 |
| Comp. Ex. 10 | (4-methylphenyl)-propyl-dimethoxysilane | 10.7 | 45.5 |
| Comp. Ex. 11 | (4-propylphenyl)-propyl-dimethoxysilane | 9.8 | 43.1 |
| Comp. Ex. 12 | (4-chlorophenyl)-propyl-dimethoxysilane | 7.5 | 42.9 |

The data reported in the above table show that the propylene polymers obtained with the aromatic silane compounds of the present invention, having a substituent in the ortho position of the aromatic ring, have unexpectedly a higher stereoblock content, with respect to the polypropylenes obtained with analogous unsubstituted compounds or with compounds bearing a substituent in a position other than ortho on the aromatic ring.

Other features, advantages and embodiments of the invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed.

The invention claimed is:

1. An aromatic silane compound having formula (I):

wherein
R$_1$ is selected from the group consisting of linear or branched C$_{1-26}$ alkyl, C$_{2-26}$ alkenyl, C$_{1-26}$ alkoxy, C$_{2-26}$ alkoxyalkyl, C$_{7-26}$ arylalkyl, C$_{3-26}$ cycloalkyl and C$_{4-26}$ cycloalkoxy groups, optionally containing one or more halogen atoms;
R$_2$ is an aromatic ring having at least one substituent in the ortho position selected from C$_{1-10}$ hydrocarbon groups with the proviso that when R$_2$ comprises a naphthyl group, R$_1$ is a linear C$_1$–C$_{26}$ alkyl; and R₃ and R₄, the same or different from each other, are selected from the group consisting of linear or branched C₁₋₁₀ alkyl and C₃₋₁₀ cycloalkyl groups.

2. The aromatic silane compound of claim 1, wherein R₁ is selected from the group consisting of linear or branched C₁₋₁₈ alkyl and C₃₋₁₈ cycloalkyl groups.

3. The aromatic silane compound of claim 2, wherein R₁ is selected from the group consisting of linear C₁₋₅ alkyl and branched C₃₋₈ alkyl groups.

4. The aromatic silane compound of claim 1, wherein R₂ is selected from the group consisting of mono-substituted phenyl, di-substituted phenyl and mono-substituted naphthyl.

5. The aromatic silane compound of claim 1, wherein R₃ and R₄ are selected from the group consisting of linear or branched C₁₋₈ alkyl and C₃₋₈ cycloalkyl groups.

6. The aromatic silane compound of claim 5, wherein R₃ and R₄ are methyl or ethyl.

7. A catalyst system for the polymerization of olefins comprising:

(A) an aromatic silane compound having formula (I):

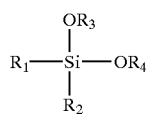

(I)

wherein
R₁ is selected from the group consisting of linear or branched C₁₋₂₆ alkyl, C₂₋₂₆ alkenyl, C₁₋₂₆ alkoxy, C₂₋₂₆ alkoxyalkyl, C₇₋₂₆ arylalkyl, C₃₋₂₆ cycloalkyl and C₄₋₂₆ cycloalkoxy groups, optionally containing one or more halogen atoms;

R₂ is an aromatic ring having at least one substituent in the ortho position with the proviso that when R₂ comprises a naphthyl group, R₁ is a linear C₁–C₂₆ alkyl; and R₃ and R₄, the same or different from each other, are selected from the group consisting of linear or branched C₁₋₁₀ alkyl and C₃₋₁₀ cycloalkyl groups;

(B) an aluminum alkyl compound; and (C) a solid catalyst component comprising Mg, Ti, halogen and an electron donor compound.

8. The catalyst system of claim 7 wherein, in said aromatic silane compound (A), R₁ is selected from the group consisting of linear or branched C₁₋₁₈ alkyl, C₁₋₁₈ alkoxyl and C₃₋₁₈ cycloalkyl groups.

9. The catalyst system of claim 8, wherein R, is selected from the group consisting of linear C₁₋₅ alkyl and branched C₃₋₈ alkyl groups.

10. The catalyst system of claim 7 wherein, in said aromatic silane compound (A), R₂ is selected from the group consisting of mono-substituted phenyl, di-substituted phenyl and mono-substituted naphthyl, and said substituent in the ortho position is selected from the group consisting of linear or branched C₁₋₁₀ alkyl and C₁₋₁₀ alkoxy groups.

11. The catalyst system of claim 7 wherein, in said aromatic silane compound (A), R₃ and R₄ are selected from the group consisting of linear or branched C₁₋₈ alkyl and C₃₋₈ cycloalkyl groups.

12. The catalyst system of claim 11, wherein R₃ and R₄ are methyl or ethyl.

13. The catalyst system of claim 7, wherein said solid component (C) comprises a titanium compound having at least one titanium-halogen bond and an internal electron donor, both supported on an active magnesium halide.

14. The catalyst system of claim 13, wherein said solid component (C) comprises the reaction product of titanium tetrachloride, active magnesium chloride and an internal electron donor.

15. A process for the polymerization of alpha-olefins comprising polymerizing propylene in the presence of the catalyst system comprising:

(A) an aromatic silane compound having formula (I):

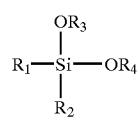

(I)

wherein
R₁ is selected from the group consisting of linear or branched C₁₋₂₆ alkyl, C₂₋₂₆ alkenyl, C₁₋₂₆ alkoxy, C₂₋₂₆ alkoxyalkyl, C₇₋₂₆ arylalkyl, C₃₋₂₆ cycloalkyl and C₄₋₂₆ cycloalkoxy groups, optionally containing one or more halogen atoms;

R₂ is an aromatic ring having at least one substituent in the ortho position with the proviso that when R₂ comprises a naphthyl group, R₁ is a linear C₁–C₂₆ alkyl; and R₃ and R₄, the same or different from each other, are selected from the group consisting of linear or branched C₁₋₁₀ alkyl and C₃₋₁₀ cycloalkyl groups;

(B) an aluminum alkyl compound; and (C) a solid catalyst component comprising Mg, Ti, halogen and an electron donor compound, to produce a polyolefin having a stereoblock content of from about 7 to about 25%.

* * * * *